United States Patent
Koch et al.

(10) Patent No.: US 11,986,242 B2
(45) Date of Patent: May 21, 2024

(54) FULL-FIELD OCT METHOD AND SYSTEM FOR GENERATING AN IMAGING OF AN OCULAR FUNDUS

(71) Applicant: Visotec GmbH, Lübeck (DE)

(72) Inventors: Peter Koch, Lübeck (DE); Gereon Hüttmann, Lübeck (DE); Helge Sudkamp, Lübeck (DE); Hendrik Spahr, Lübeck (DE); Dierck Hillmann, Lübeck (DE); Michael Münst, Lübeck (DE)

(73) Assignee: Visotec GmbH, Lübeck (DE)

( * ) Notice: Subject to any disclaimer, the term of this patent is extended or adjusted under 35 U.S.C. 154(b) by 968 days.

(21) Appl. No.: 16/965,206

(22) PCT Filed: Jan. 23, 2019

(86) PCT No.: PCT/EP2019/051601
§ 371 (c)(1),
(2) Date: Jul. 27, 2020

(87) PCT Pub. No.: WO2019/145348
PCT Pub. Date: Aug. 1, 2019

(65) Prior Publication Data
US 2021/0038074 A1    Feb. 11, 2021

(30) Foreign Application Priority Data
Jan. 26, 2018   (EP) ...................... 18153564

(51) Int. Cl.
*A01B 3/12*    (2006.01)
*A61B 3/10*    (2006.01)
(Continued)

(52) U.S. Cl.
CPC ............ *A61B 3/1225* (2013.01); *A61B 3/102* (2013.01); *G01B 9/02032* (2013.01);
(Continued)

(58) Field of Classification Search
CPC ......... A61B 3/1225; A61B 3/102; B61B 3/00; G01B 9/02091; G01B 9/02075;
(Continued)

(56) References Cited

U.S. PATENT DOCUMENTS

| 10,732,354 | B2 * | 8/2020 | Yi ...................... G02B 6/29388 |
| 11,019,993 | B2 * | 6/2021 | Higuchi ............... A61B 5/0066 |

(Continued)

FOREIGN PATENT DOCUMENTS

| CN | 1426286 A | 6/2003 |
| DE | 102015113465 A1 | 2/2017 |

(Continued)

OTHER PUBLICATIONS

"Aberration-free volumetric high-speed imaging of in vivo retina"; Dierck Hillman, et al.; Scientific Reports | 6:35209 | DOI: 10.1038/srep35209; Published: Oct. 20, 2016; 11 pgs.

(Continued)

*Primary Examiner* — Hoa Q Pham
(74) *Attorney, Agent, or Firm* — Alix, Yale & Ristas, LLP

(57) ABSTRACT

The invention relates to a full-field OCT method for generating an imaging of an ocular fundus (31), in which short-coherent light (22) is emitted and split into an object beam path (25) and a reference beam path (24). The object beam path (25) is directed onto the ocular fundus (33). The reference beam path (24) and a portion of the object beam path (25) reflected by the ocular fundus (31) are directed onto an image sensor (32), such that an interference between the reference beam path (24) and the object beam path (25) occurs on the image sensor (32), wherein the reference beam path (24) impinges on the image sensor (32) at an angle deviating from the object beam path (25). Before impinging on the image sensor (32), the reference beam path (24)

(Continued)

impinges on an optical correction element (27) in order to reduce a chromatic aberration within the reference beam path (24). Intensity information and phase information is determined from a capturing of the image sensor. A focus-adjusted image of the ocular fundus is calculated. The invention also relates to a system that is suitable for carrying out said method. Images of the ocular fundus can be captured without the beam path being previously adapted to the refractive power of the eye lens.

13 Claims, 3 Drawing Sheets

(51) Int. Cl.
    *A61B 3/12*     (2006.01)
    *G01B 9/02015*     (2022.01)
    *G01B 9/02055*     (2022.01)
    *G01B 9/02056*     (2022.01)
    *G01B 9/02091*     (2022.01)

(52) U.S. Cl.
    CPC ..... *G01B 9/02058* (2013.01); *G01B 9/02075* (2013.01); *G01B 9/02091* (2013.01)

(58) Field of Classification Search
    CPC .............. G01B 9/02032; G01B 9/0209; G01B 9/02058; G01B 11/2441; G01J 3/0208; G06T 11/003; G06T 2207/10101
    USPC ........ 356/124–127, 456, 497, 479, 511, 499, 356/450, 521, 488, 494; 351/206, 221; 381/131
    See application file for complete search history.

(56) References Cited

U.S. PATENT DOCUMENTS

| | | | |
|---|---|---|---|
| 2007/0024856 A1* | 2/2007 | Izatt | ................... G01B 9/02044 356/497 |
| 2007/0038040 A1 | 2/2007 | Cense et al. | |
| 2008/0192783 A1 | 8/2008 | Rathjen et al. | |
| 2010/0020328 A1 | 1/2010 | Huettmann et al. | |
| 2010/0253907 A1 | 10/2010 | Korb et al. | |
| 2011/0116045 A1* | 5/2011 | Utagawa | ................ A61B 3/102 351/210 |
| 2015/0055090 A1 | 2/2015 | Cense et al. | |
| 2018/0235461 A1 | 8/2018 | Koch et al. | |

FOREIGN PATENT DOCUMENTS

| | | |
|---|---|---|
| EP | 1887312 A1 | 2/2008 |
| FR | 2943145 A1 | 9/2010 |
| JP | 2012508366 A | 4/2012 |
| WO | 0182791 A1 | 11/2001 |
| WO | 2010053979 A2 | 5/2010 |
| WO | 2013141229 A1 | 9/2013 |
| WO | 2015042093 A1 | 3/2015 |
| WO | 2016187675 A1 | 12/2016 |
| WO | 2017029160 A1 | 2/2017 |

OTHER PUBLICATIONS

Chinese Search Report for Application No. 2019800103691 filed Jan. 23, 2019, dated Jan. 16, 2023, 3 pgs.

PCT International Search Report for International application No. PCT/EP2019/051601 dated Apr. 9, 2019; 2 pgs.

Hillmann et al., "Aberration-free volumetric high-speed imaging of in vivo retina"; Scientific Reports, 6:35209, Doi: 10.1038/SREP35209, www.nature.com/scientificreports; pp. 1-11.

J.W. Goodman, "Chapter 9—Holography—Introduction to Fourier Optics", 1996; cited in Paragraph [0010] of Specification filed on Jul. 27, 2020; 98 pgs.

Schnars U, Jueptner W , "Digital Holography", 2010; Berlin, Heidelberg: Springer; cited in Paragraph [0010] of Specification filed Jul. 27, 2020; 15 pgs.

\* cited by examiner

FULL-FIELD OCT METHOD AND SYSTEM FOR GENERATING AN IMAGING OF AN OCULAR FUNDUS

BACKGROUND

The invention relates to a full-field OCT method and a full-field OCT system for generating an image representation of an ocular fundus.

The ocular fundus of a human eye can be examined using optical coherence tomography (OCT). It is possible to obtain image information about tissue structures situated below the surface. In an OCT measurement, short-coherent light is split into an object beam path and a reference beam path. The object beam path is guided onto the ocular fundus. Part of the object beam path reflected by the ocular fundus is made to interfere with the reference beam path. Information about the depth position of a scattering center in the tissue of the ocular fundus can be obtained from the reference pattern.

In conventional OCT imaging, the object is scanned using an OCT beam in order to obtain a planar image (en-face image). Full-field OCT differs from these conventional OCT methods in that use is made of an image sensor, which records an en-face image with one recording.

DE 10 2015 113 465 A1 has described a full-field OCT method for examining the ocular fundus, in which the object beam path and the reference beam path are made to interfere on an image sensor. The reference beam path strikes the image sensor at a different angle such that intensity information and phase information can be derived from the measured values of the image sensor. A single recording of the image sensor yields an en-face section of the object. By altering the length of the optical path in the reference beam path, it is possible to obtain slice images from different depth positions. The slice images can be put together to form a three-dimensional image.

In DE 10 2015 113 465 A1, the optical elements in the object beam path are adjusted in such a way that the ocular fundus is imaged in focus on the image sensor. Prior to each measurement of a different eye, the object beam path must be readjusted in order to obtain a sharp image representation on the image sensor. This is because the object beam path passes through the refractive elements (lens, cornea) of the eye. Since the imaging properties of the refractive elements are not the same for all eyes, a defocused and hence out-of-focus image would arise on the image sensor without an adjustment.

A further full-field OCT method is described in Hillmann et al., Aberration-free volumetric highspeed imaging of in vivo retina, Scientific Reports—6:35209—DOI: 10.1038/srep35209, pages 1-11, October 2016, published at www.nature.com/scientificreports.

SUMMARY OF THE INVENTION

The invention is based on the object of presenting a full-field OCT method and system, which require less effort to record an image of the ocular fundus. Proceeding from the prior art specified, the object is achieved by the features of the independent claims. Advantageous embodiments are specified in the dependent claims.

Short-coherent light is emitted in the method according to the invention. The short-coherent light is split into an object beam path and a reference beam path, wherein the object beam path is guided onto the ocular fundus. The reference beam path and part of the object beam path reflected by the ocular fundus are guided to an image sensor such that interference between the reference beam path and the object beam path arises on the image sensor. The reference beam path strikes the image sensor at an angle that deviates from the object beam path. Prior to the incidence on the image sensor, the reference beam path strikes an optical correction element in order to reduce a chromatic deviation within the reference beam path. Intensity information and phase information are ascertained from the recording of the image sensor and a focus-corrected image of the ocular fundus is calculated.

Thus, the invention proposes compensating an imaging aberration in the full-field OCT measurement not by way of an adjustment of optical elements in the object beam path but by way of a correction calculation. The invention allows an adjustment of optical elements in the object beam path to be dispensed with. This simplification allows an image representation of the ocular fundus to be recorded even by persons who have no knowledge of optical beam paths.

That the availability of intensity information and phase information allows in principle a focusing error of an individual light wave to be eliminated by way of calculation is textbook knowledge (J. W. Goodmann: Introduction to Fourier Optics; Schnars U, Jueptner W (2010). Digital Holography (Berlin, Heidelberg: Springer)). It is not possible to directly apply such computational correction methods to full-field OCT measurements for the reasons set forth below.

A complete image is recorded in one recording in the case of a full-field OCT measurement according to DE 10 2015 113 465 A1. Thus, in contrast to an individual light wave, spatially resolved information can be included in the correction calculation. Taking account of the spatially resolved information is made more difficult because the deviating angles at which the object beam path and the reference beam path are incident on the image sensor are often accompanied by a chromatic deviation. This applies, in particular, if the object beam path is not focused in the plane of the image sensor. The interference term is encoded with a carrier frequency as a result of the angle between the reference beam path and the object beam path. However, the carrier frequency is dependent on the wavelength, leading to chromatic smearing in frequency space. This prevents an effective correction.

The invention has recognized that the chromatic smearing can be undone by an optical correction element in the reference beam path. When applying the method according to the invention, the computational elimination of a focusing error is no longer complicated by chromatic smearing.

In contrast to full-field OCT, computational elimination of a focusing error is not possible in scanning OCT because scanning OCT does not supply phase information with sufficient quality according to the current state of measurement technology.

The method according to the invention can be carried out in such a way that the object beam path is incident on the image sensor at right angles. Then, the angle included between the reference beam path and the plane of the array is not a right angle. Embodiments in which the object beam path does not strike the image sensor at right angles are also possible.

A beam splitter, through which the short-coherent light passes, can be used to split the short-coherent light into the object beam path and the reference beam path. The beam splitter can be disposed in such a way that the object beam path and/or the reference beam path passes through the beam splitter twice with different directions of propagation. The object beam path can be cast back in the direction of the beam splitter by the ocular fundus.

A reflection element used to deflect the reference beam path and, in particular, used to cast said reference beam path back in the direction of the beam splitter can be disposed in the reference beam path. The reference beam path upstream of the reflection element can be separated from the reference beam path downstream of the reflection element such that there is no intersection between the beam path arriving at the reflection element and the beam path emanating from the reflection element. This relates to a section of the reference beam path adjacent to the reflection element. At a greater distance from the reflection element, the opposing sections of the reference beam path can overlap again. The reflection element can be a prism, in particular a roof prism. A plane extending through the roof edge of the prism can be disposed between the arriving part and the emanating part of the reference beam path.

The length of the optical path of the reference beam path can be alterable. In particular, the length of the optical path of the reference beam path can be alterable without the length of the optical path of the object beam path being altered at the same time. By way of example, it could be possible to displace the reflection element such that the distance between the reflection element and the beam splitter is altered. If the distance between the reflection element and the beam splitter is increased, the reference beam path passes over the lengthened path twice on the way from the beam splitter to the reflection element and back again. By altering the length of the optical path in the reference beam path, it is possible to set the depth position at which scattering centers can be discovered in the tissue of the ocular fundus. The method can be carried out in such a way that en-face sections are recorded at a plurality of depth positions. The plurality of the en-face sections can be put together to form a three-dimensional image representation of the ocular fundus.

The optical correction element can be disposed between the beam splitter and the reflection element. The optical correction element can be disposed in such a way that the reference beam path passes through the optical correction element only once. In particular, the passage through the optical correction element can be implemented between the reflection element and the beam splitter in the reference beam path.

The optical correction element can be a transmission grating. In the case of a transmission grating, the reference beam path can pass through the optical correction element. It is also possible to design the optical correction element as a reflection grating. In this case, the reference beam path can be reflected at the optical correction element. The transmission grating and the reflection grating can comprise grating lines aligned perpendicular to a plane which the object beam path and the reference beam path span between the beam splitter and the eye and the reflection element, respectively.

The transmission grating can be designed such that it brings about a deflection of the reference beam path of between 1° and 5°, preferably between 2° and 4°. The transmission grating or reflection grating can have between 25 and 100 grating lines per millimeter, preferably between 500 and 80 grating lines per millimeter.

In particular, the reduction in the chromatic deviation can emerge from the pulse front of the reference beam path emerging from the optical correction element deviating from the propagation direction of the reference beam path. In particular, the optical correction element can be set such that the normal of the pulse front of the reference beam path emerging from the optical correction element includes an angle with the propagation direction of the object beam path that is smaller than the angle between the propagation direction of the reference beam path and the propagation direction of the object beam path. In particular, the normal of the pulse front of the reference beam path emerging from the optical correction element can be parallel to the propagation direction of the object beam path.

As a result of such an optical structure of the full-field OCT system, an interference pattern within the individual pixels (speckle) arises on the image sensor, from which it is possible to ascertain both the amplitude of the backscattering at the corresponding depth and the associated phase angle; see DE 10 2015 113 465 A1. In the case of ideal imaging of the object beam path which extends through the lens of the human eye and the optical elements of the full-field OCT structure, the spherical wave emitted by an object point on the ocular fundus is converted into a convergent spherical wave which forms an image point on the image sensor.

By way of example, the object beam path of the full-field OCT system can be configured in such a way that ideal imaging on the image sensor sets in when an object point of the ocular fundus is imaged to infinity by the refractive elements of the eye (lens and cornea). Below, the refractive elements of the eye are collectively referred to as lens of the eye. In the case of a refractive error of the patient, the lens of the eye does not image to infinity or from infinity, but into a plane in front of or behind the eye. For the object beam path of the full-field OCT system, such an aberration means that the image plane lies in front of or behind the image sensor.

It is known from Fourier optics that aberrations can be represented as phase errors. Imaging aberrations lead to a deformation of the phase front of the light in the beam path. A focusing error, i.e., imaging into the wrong image plane, can be represented as a second order Zernike polynomial, and so the focusing error leads to a quadratic phase factor. Higher-order aberrations, such as spherical aberrations or astigmatism, can be represented as accordingly more complicated functions. The method according to the invention can be carried out in such a way that not only imaging into the wrong image plane but also higher-order aberrations are corrected. In particular, an astigmatism can be corrected.

In a paraxial approximation, the spherical wavefronts emanating from an object point are approximated by a parabolic wavefront. Accordingly, the parabolic wavefronts can be converted into a plane wavefront or into a convergent wavefront with any radius by way of a quadratic phase factor. If the quadratic phase factor is too small or too large, the object is not imaged correctly into the image plane. Then, the rays of an object point meet in front of or behind the image plane. Accordingly, the object point appears washed out in the image plane.

Since it is not only the intensities but also the phases that are measured within the scope of full-field OCT, it is possible to numerically eliminate the phase errors arising from the focusing error. To this end, the image data are Fourier-transformed and the phase factor is added in Fourier space. The spectrum altered thus is then transformed back into real space, where a refocused (sharp) image of the object is obtained. Using these steps, it is possible to calculate a focus-corrected image of the ocular fundus.

In the simplest case, the refractive error of the patient is known. Then, the phase factor required for the correction can be determined directly from the refractive error in diopter. For the defocus, this is the quadratic phase factor $\phi_{Defokus}$, which can be calculated for the radius $r_{Apertur}$ by $$\Phi_{Defokus}(i, j) = \frac{D \cdot \pi \cdot r_{Apertur}^2}{\lambda}$$

Here, D is the refractive error in diopter and $\lambda$ is the central wavelength of the measurement system. Accordingly, the calculation of a focus-corrected image of the ocular fundus according to the invention can be simplified by virtue of using the known refractive error of the patient to derive a phase factor used during the correction.

Accordingly, once image data have been recorded with the image sensor, it is possible to perform a calculation which is used to calculate a focus-corrected image of the ocular fundus from the image data. The calculation can be carried out in a computing unit that is distant from the recording device. The image data can be transmitted to the computing unit via a data connection.

Computational elimination of a focusing error assumes that the phase angle is maintained during the recording of the image to be corrected. In living samples, the phase relationship is lost within a short period of time as a result of the movements of the sample. By way of example, for the ocular fundus, the phase angle is typically only maintained for a few 100 µs. In the method according to the invention, a complete image of the object plane (en-face section) can be recorded within a period of less than 800 µs, preferably less than 500 µs, more preferably less than 300 µs. In particular, the complete image can be captured within a single exposure time of the image sensor.

The image sensor can comprise a multiplicity of pixels which, for example, could be arranged in the form of a rectangular array. The number of pixels along one dimension of the rectangle could range, for example, between 500 and 5000, preferably between 100 and 3000. The width of an individual pixel could range, for example, between 1 µm and 8 µm, preferably between 2 µm and 5 µm. The light source with which the short-coherent light is generated can be a superluminescent diode, for example.

The method can be carried out in such a way that the optical elements of the employed apparatus that are disposed in the object beam path are rigid. Expressed differently, it is not possible within the scope of normal operation of the apparatus to displace the image plane by adjusting optical elements of the apparatus in the object beam path. This does not preclude an adjustment occurring outside of normal operation, for example during production or maintenance of the apparatus. Dispensing with an adjustment option makes it easier for untrained staff to carry out measurements.

A fixation light can be directed on the eye of the patient in order to provide the patient with an orientation for the viewing direction during the recording. The patient can look in the direction of the fixation light and consequently adopt a viewing direction suitable for the recording.

If focusing the object beam path into the image plane is dispensed with in the method according to the invention, this may have effects on the fixation light, to the extent of the fixation light not being sharply visible to the patient. Therefore, the use of a focus-independent fixation light may be advantageous for the method according to the invention. A fixation light is referred to as focus-independent if a sharp perception of the fixation light is possible without an image plane of the fixation light being brought into correspondence with the retina of the patient's eye. An example of a focus-independent fixation light is a laser beam that, with a small diameter, is directed onto the eye. Such a laser beam is always perceived as a sharp spot by the eye, independently of the distance between the light source and the eye. There are other options for generating a focus-independent fixation light, for example by virtue of the light of a light source being guided through a conical lens (axicon) or a hollow cylinder.

A method in which a focus-independent fixation light is used has independent inventive content even if allowing the reference beam path to pass through an optical correction element prior to incidence on the image sensor in order to reduce a chromatic deviation within the reference beam path is dispensed with. In contrast to conventional measurement methods on the eye, in which both the measurement per se and the sharp perception of the fixation light require the patient to correctly set the viewing direction and the focus, the patient can concentrate on the viewing direction only within the scope of this method. The invention has recognized that this allows the avoidance of measurement errors arising from the patient being asked to simultaneously concentrate on the viewing direction and the focus. It was found that patients who find correctly setting the focus difficult also tend to change the viewing directions. It is now easier for these patients because possible difficulties with setting the focus cease to apply.

The invention moreover relates to a full-field OCT system having a recording device and a computing unit. The recording device comprises a light source for emitting short-coherent light and a beam splitter for splitting the short-coherent light into an object beam path and a reference beam path. The object beam path is guided to an exit opening of the recording device. The reference beam path and part of the object beam path reflected by an object are made to interfere on an image sensor, wherein the reference beam path strikes the image sensor at an angle deviating from the object beam path and wherein the reference beam path strikes an optical correction element prior to the incidence on the image sensor in order to reduce a chromatic deviation within the reference beam path. The computing unit is designed to calculate a focus-corrected image of the object from image data recorded with the image sensor.

The recording device in the system according to the invention can be used, in particular, to generate an image representation of a rear eye section of a human eye. The recording device can be configured as a hand-held device designed to be held by the patient themselves, the image representation being recorded of the eye of said patient. The hand-held device can be configured in such a way that the optical elements of the object beam path cannot be adjusted during normal operation of the hand-held device. The computing unit can be disposed at a distance from the hand-held device. Provision can be made of a data line, by means of which image data can be transferred from the hand-held device to the computing unit.

The system can be developed with further features which are described in the context of the method according to the invention. The method can be developed with further features which are described in the context of the system according to the invention.

BRIEF DESCRIPTION OF THE DRAWINGS

In the following, the invention is described in exemplary fashion on the basis of advantageous embodiments, with reference being made to the attached drawings. In detail.

DETAILED DESCRIPTION

Figure 1:
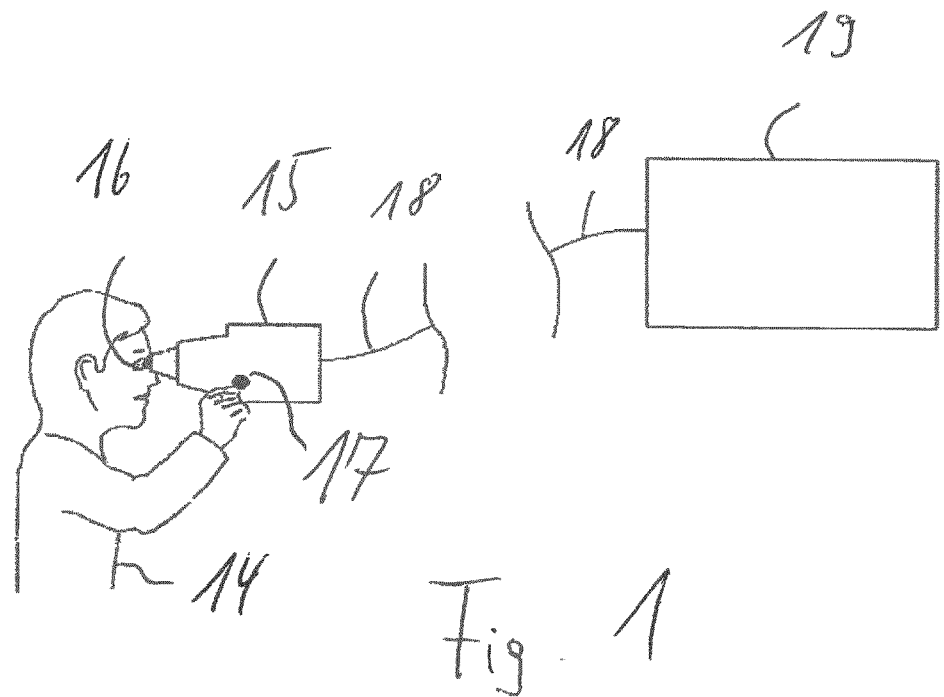
FIG. 1: shows a schematic illustration of a full-field OCT system according to the invention.

In the full-field OCT system according to the invention shown in FIG. 1, a patient 14, whose ocular fundus is the subject of imaging, holds a hand-held device 15 in the hand. The hand-held device 15 is disposed in front of the eye 16 of the patient 14 such that the patient 14 can see a fixation light in the interior of the hand-held device 15. Once the patient 14 has set their viewing direction on the basis of the fixation light, they actuate a switch 17 that is used to trigger the recording of an image representation of the ocular fundus.

Once the recording has been completed, the image data are transferred via a data network 18 to a central computer 19 that is distant from the patient 14. By way of example, the central computer 19 can be disposed at the headquarters of a service provider who operates the full-field OCT system. The system can be configured such that the central computer 19 receives image data from a multiplicity of hand-held devices 15, which are operated at different locations or in different installations. In particular, the computing steps required for a possibly required focus correction can be carried out on the central computer 19. In alternative embodiments of the invention, the hand-held device 15 itself is designed to carry out the computing steps for the focus correction.

Figure 2:
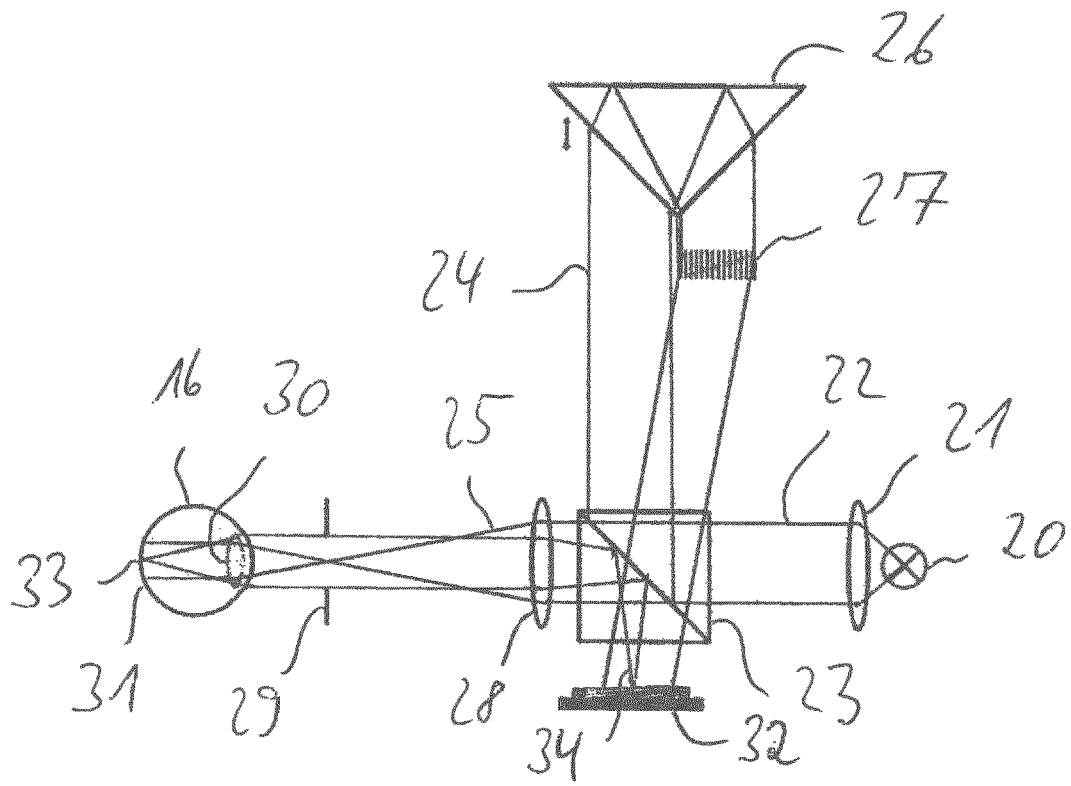
FIG. 2: shows an illustration of the beam paths of the hand-held device of FIG. 1.

According to FIG. 2, the hand-held device 15 comprises a superluminescent diode 20, which emits short-coherent light with a coherence length of 10 μm, for example. A first lens 21 is used to generate a collimated beam path 22 of the short-coherent light, which is incident on a beam splitter 23. The beam splitter 23 is used to split the short-coherent light 22 into a reference beam path 24 and an object beam path 25.

The reference beam path 24 is incident on a roof prism 26, enters the prism 26 through a roof face, is reflected at a hypotenuse face of the prism 26 and emerges from the roof prism 26 again in the opposite direction, through the other roof face but with a parallel offset. The reference beam path 24 is incident on a transmission grating 27 and guided back in the direction of the beam splitter 23 by the transmission grating 27.

Proceeding from the superluminescent diode 20, the object beam path 25 passes through the beam splitter 23 and is guided to the eye 16 of the patient via a second lens 28 and a stop 29. The object beam path 25 passes through the lens of the eye 30 into the interior of the eye 16 and illuminates the ocular fundus 31 over an area.

Components of the short-coherent light 22 cast back by the ocular fundus 31 return to the beam splitter 23 via the lens of the eye 30 and the second lens 28, the object beam path being deflected in the direction of an image sensor 32 at said beam splitter. The optical elements in the object beam path 25 are disposed in such a way that the ocular fundus 31 is imaged onto the image sensor 32. This is illustrated in FIG. 2 using the example of an object point 33, which corresponds to an image point 34 on the image sensor 32.

The reference beam path 24 is overlaid on the object beam path 25 between the beam splitter 23 and the image sensor 32. There is interference between the object beam path 25 and the reference beam path 24 in the plane of the image sensor 32. The interference pattern is recorded using the image sensor 32.

There is an angle between the object beam path 25 and the reference beam path 24 upon incidence on the image sensor 32. The object beam path 25 strikes the image sensor 32 at right angles. When striking the image sensor 32, the reference beam path 24 includes an angle of slightly less than 90° with the image sensor 32, for example an angle of 87°.

The direction of the reference beam path 24 is set by the transmission grating 27. Before passing through the transmission grating 27, the reference beam path 24 propagates in a direction that is at right angles to the image sensor 32. The reference beam path 24 changes its propagation direction when passing through the transmission grating 27. Here, the transmission grating 27 is designed in such a way that a chromatic deviation is avoided. Expressed differently, the transmission grating 27 is designed in such a way that the pulse front of the reference beam path 24 emerging from the transmission grating 27 is parallel to the image sensor 32. Accordingly, the pulse front is not at right angles to the propagation direction of the reference beam path but includes a different angle with the direction of the reference beam path 24. The transmission grating 27 forms an optical correction element within the meaning of the invention, by means of which a chromatic deviation within the reference beam path 24 is reduced.

This avoids smearing in Fourier space of the multispectral wave field emanating from an object point 33. This also applies if, unlike what is shown in FIG. 2, the object beam path 25 is not focused on the image sensor 32 but has a focusing error. Accordingly, the focus-corrected image can be calculated without the result being impaired by chromatic smearing.

FIG. 2 shows an object beam path 25 in which the object point 33 is imaged to infinity by the lens of the eye 30. Thus, the eye 16 does not have a refractive error. The hand-held device 15 is adjusted in such a way that there is focused imaging onto the image sensor 32 when the eye 16 does not have a refractive error.

A focusing error arises in the case of a refractive error of the eye 16, within the scope of which the image plane does not correspond to the image sensor 32 but is located in a plane in front of or behind the image sensor 32. An image recorded by the image sensor 32 appears blurred.

Figure 3:
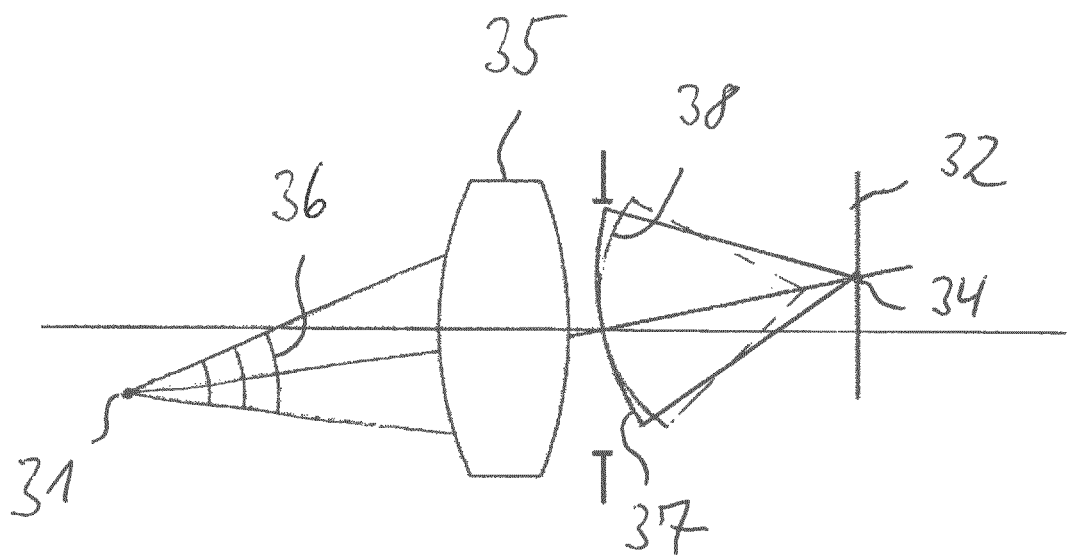
FIG. 3: shows a schematic illustration of the calculation of a focus-corrected image.

The steps for correcting the focusing error are explained on the basis of FIG. 3. Each object point 31 of the ocular fundus 33 can be considered to be the starting point of a divergent spherical wave 36. The divergent spherical wave 36 is converted into a convergent spherical wave 37 by the lens of the eye 30 and the second lens 28, which are illustrated together as a lens component 35 in FIG. 3. In the case of a lens of the eye without a refractive error, the convergent spherical wave 37 opens into an image point 34 on the image sensor 32.

If the eye 16 has a refractive error, the convergent spherical wave does not have the correct angle of curvature following the lens component 35 and the image point lies either in front of the image sensor 32 or behind the image sensor 32. In FIG. 3, this is illustrated on the basis of a convergent spherical wave 38, which is curved too strongly and the image point of which is located in front of the image sensor 32.

In order to generate a focus-corrected image of the ocular fundus 33 in the case of such a focusing error, the washed-out image data recorded by the image sensor 32 are initially transmitted to the central computer 19. The central computer 19 subjects the image data to a Fourier transform so that a suitable phase factor can be added in Fourier space. The spectrum altered thus is then transformed back into real space, where a refocused (sharp) image of the object is obtained. Since the reference beam path 24 was chromatically corrected by the transmission grating 27, the correction calculation can be performed together for all wavelengths contained in the short-coherent light 22.

Figure 4:
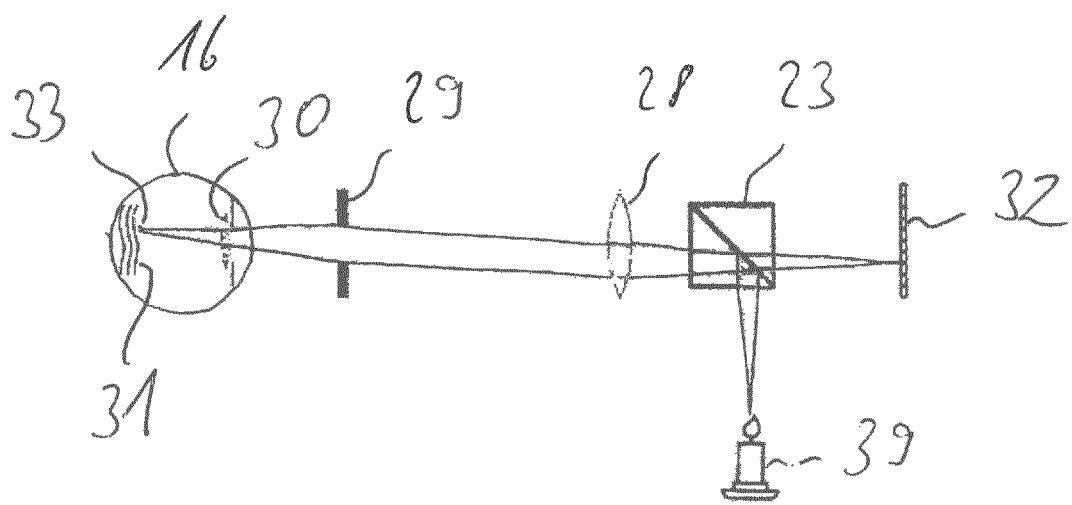
FIG. 4: shows another aspect of the hand-held device of FIG. 2.

FIG. 4 illustrates the fixation light 39 of the hand-held device 15. The lens of the eye 30 images the object point 33 from the ocular fundus 31 to infinity, and so the eye does not have a refractive error. The fixation light 39 is disposed in such a way that it is perceived in focus by an eye 16 without a refractive error.

Figure 5:
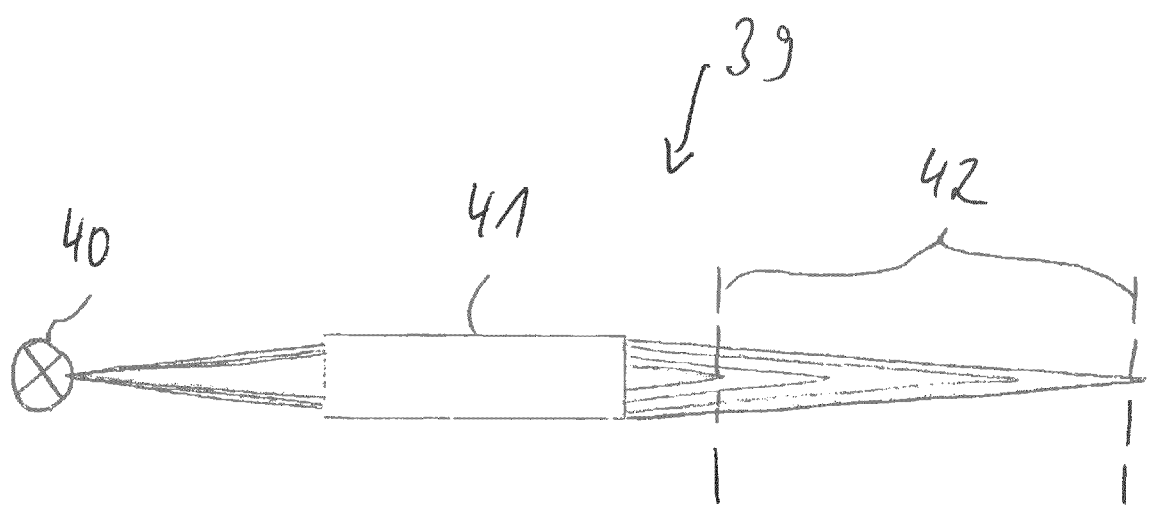
FIG. 5: shows an embodiment of a focus-independent fixation light.

FIG. 5 shows an embodiment of a fixation light 39 which can be perceived in focus at different axial positions. The light emitted by a light source 40 is guided into a hollow cylinder 41, which is dimensioned in such a way that each light ray is reflected precisely once in the interior of the hollow cylinder 41. An axial section of the length 42, in which the light can be perceived as a sharply delimited spot, arises on the other side of the hollow cylinder 41. This is an example for a focus-independent fixation light 39, which can also be perceived in focus by a patient with a refractive error without needing an adjustment of optical elements within the hand-held device 15.

The invention claimed is:

1. A full-field OCT method for generating an image representation of an ocular fundus, including the following steps:
   a. emitting short-coherent light;
   b. splitting the short-coherent light into an object beam path and a reference beam path, wherein the object beam path is guided onto the ocular fundus;
   c. guiding the reference beam path and part of the object beam path reflected by the ocular fundus onto an image sensor such that interference between the reference beam path and the object beam path arises on the image sensor, wherein the reference beam path strikes the image sensor at an angle that deviates from the object beam path and wherein, prior to the incidence on the image sensor, the reference beam path strikes an optical correction element in order to reduce a chromatic deviation within the reference beam path;
   d. ascertaining intensity information and phase information from a recording of the image sensor;
   e. calculating a focus-corrected image of the ocular fundus from the ascertained intensity information and phase information.

2. The full-field OCT method of claim 1, wherein the direction of the reference beam path is deflected using a reflection element.

3. The full-field OCT method of claim 2, wherein the reference beam path upstream of the reflection element is separated from the reference beam path downstream of the reflection element.

4. The full-field OCT method of claim 2, wherein the optical correction element is disposed between a beam splitter and the reflection element.

5. The full-field OCT method of claim 1, wherein a length of an optical path of the reference beam path is alterable.

6. The full-field OCT method of claim 1, wherein the optical correction element is embodied as a transmission grating or as a reflection grating.

7. The full-field OCT method of claim 1, wherein the optical correction element is set such that a normal of a pulse front of the reference beam path emerging from the optical correction element includes an angle with a propagation direction of the object beam path that is smaller than an angle between a propagation direction of the reference beam path and the propagation direction of the object beam path.

8. The full-field OCT method of claim 1, wherein a phase factor used when calculating the focus-corrected image is derived from a known refractive error of the patient.

9. The full-field OCT method of claim 1, wherein the image sensor is designed to record an en-face section within a period of less than 800 µs, preferably less than 500 µs, further preferably less than 300 µs.

10. The full-field OCT method of claim 1, wherein the optical elements disposed in the object beam path are rigid.

11. The full-field OCT method of claim 1, comprising a fixation light, which the patient sees during the recording.

12. The full-field OCT method of claim 11, wherein the fixation light is a focus-independent fixation light.

13. A full-field OCT system comprising a recording device and a computing unit, the recording device comprising a light source for emitting short-coherent light, a beam splitter for splitting the short-coherent light into an object beam path and a reference beam path, wherein the object beam path is guided to an exit opening of the recording device, and comprising an image sensor, on which the reference beam path and part of the object beam path reflected by an object are made to interfere, wherein the reference beam path strikes the image sensor at an angle deviating from the object beam path and wherein the reference beam path strikes an optical correction element prior to the incidence on the image sensor in order to reduce a chromatic deviation within the reference beam path, and wherein the computing unit ascertains intensity and phase information from image data recorded with the image sensor and calculates a focus-corrected image of the object from the ascertained intensity information and phase information.

* * * * *